(12) United States Patent
Vaccaro

(10) Patent No.: US 10,582,736 B2
(45) Date of Patent: Mar. 10, 2020

(54) WIREFORM ATTACHMENT MECHANISM

(71) Applicant: Safariland, LLC, Jacksonville, FL (US)

(72) Inventor: Dylan Vaccaro, Jacksonville, FL (US)

(73) Assignee: Safariland, LLC, Jacksonville, FL (US)

( * ) Notice: Subject to any disclaimer, the term of this patent is extended or adjusted under 35 U.S.C. 154(b) by 124 days.

(21) Appl. No.: 15/871,299

(22) Filed: Jan. 15, 2018

(65) Prior Publication Data

US 2018/0199652 A1 Jul. 19, 2018

Related U.S. Application Data

(60) Provisional application No. 62/446,692, filed on Jan. 16, 2017, provisional application No. 62/485,085, filed on Apr. 13, 2017.

(51) Int. Cl.
| | |
|---|---|
| *A42B 3/04* | (2006.01) |
| *A63B 71/10* | (2006.01) |
| *A42B 3/00* | (2006.01) |
| *A42B 3/16* | (2006.01) |
| *A61F 11/14* | (2006.01) |

(52) U.S. Cl.
CPC ............... *A42B 3/04* (2013.01); *A42B 3/003* (2013.01); *A42B 3/166* (2013.01); *A63B 71/10* (2013.01); *A61F 2011/145* (2013.01)

(58) Field of Classification Search
CPC ........... A42B 3/04; A42B 3/003; A42B 3/166; A63B 71/10
USPC ............................................................. 2/422
See application file for complete search history.

(56) References Cited

U.S. PATENT DOCUMENTS

| | | | | | |
|---|---|---|---|---|---|
| 4,209,264 | A | * | 6/1980 | Hellberg | A42B 3/166 403/80 |
| 5,546,610 | A | * | 8/1996 | Herzig | A42B 3/225 2/422 |
| 2003/0079275 | A1 | | 5/2003 | Woo | |
| 2011/0225705 | A1 | * | 9/2011 | Fernandes | A42B 3/166 2/209 |
| 2013/0219598 | A1 | * | 8/2013 | Pfanner | A42B 3/16 2/423 |
| 2016/0324248 | A1 | * | 11/2016 | Winters | A42B 3/30 |
| 2018/0168270 | A1 | * | 6/2018 | Vaccaro | H04R 1/1066 |
| 2018/0199652 | A1 | * | 7/2018 | Vaccaro | A42B 3/166 |

FOREIGN PATENT DOCUMENTS

| | | |
|---|---|---|
| DE | 1912241 U | 3/1965 |
| DE | 2260311 A1 | 6/1973 |
| GB | 1456956 A | 12/1976 |

OTHER PUBLICATIONS

European Patent Application No. 18151829.1—European Search Report filed May 11, 2018.

* cited by examiner

*Primary Examiner* — Gloria M Hale
(74) *Attorney, Agent, or Firm* — Kane Kessler, P.C.; Paul E. Szabo

(57) ABSTRACT

A wireform attachment mechanism, or support arm, that can be used to attach an earcup to a helmet. The outer end of the support arm can be opened to release the earcup, or closed to clamp onto the earcup.

7 Claims, 14 Drawing Sheets

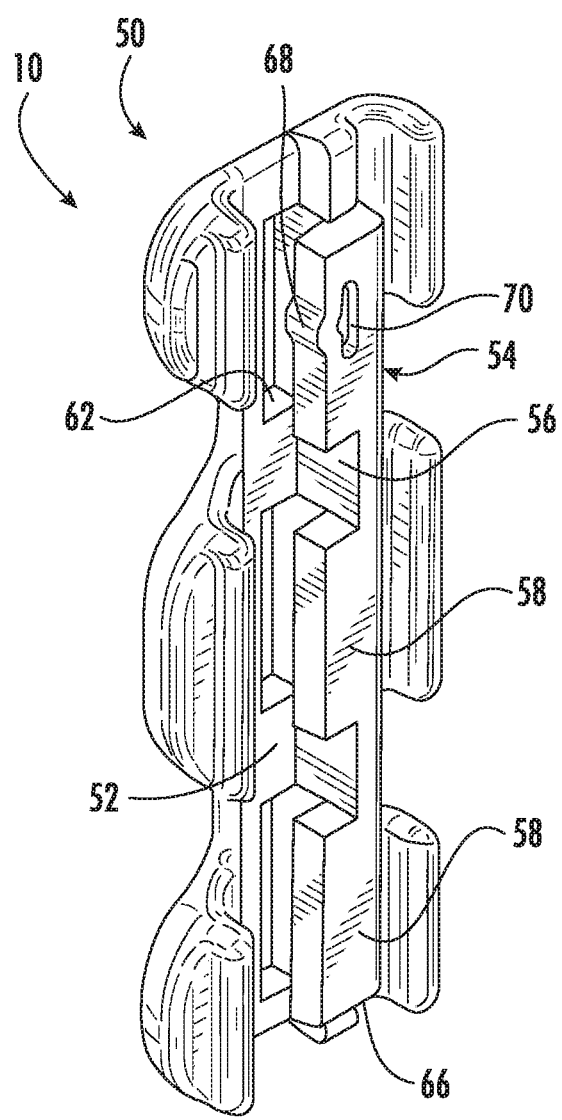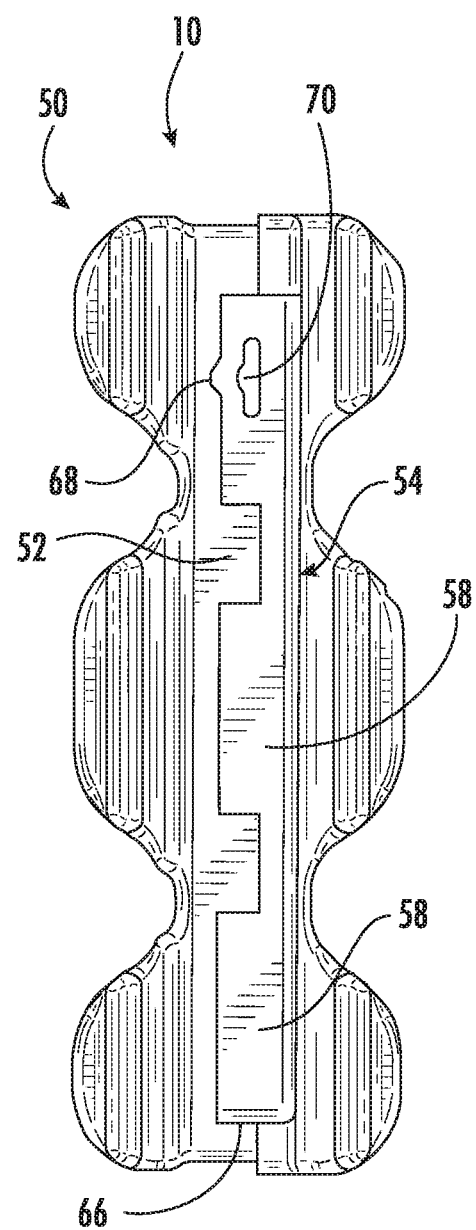
FIG. 3A                FIG. 3B
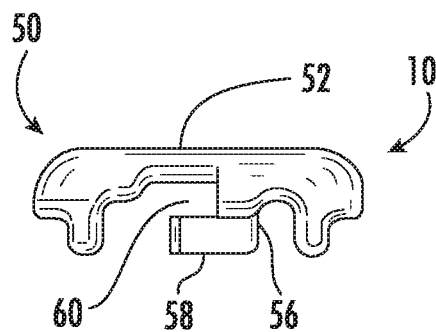
FIG. 3C

WIREFORM ATTACHMENT MECHANISM

RELATED APPLICATION

U.S. application Ser. No. 15/846,604, filed Dec. 19, 2017, now published as U.S. Patent Application Publication No. U.S. 2018/0168270 A1, and titled "Rail Connector For Earcup Suspension Assembly", is a related application Said related application discloses a rail connector of the type disclosed in this current application.

BACKGROUND OF THE INVENTION

This invention relates to a wireform attachment mechanism, or support arm, that can be used to attach an item to a support. The outer end of the support arm can selectively clamp onto an item. The outer end can be opened to release the item, or closed to clamp onto the item.

The support arm can be used in various different applications. In one application, the support arm is used in association with a headset that includes earcups designed to overlie and seal around the wearer's ears. This type of headset is often worn with a protective helmet of a soldier or a fire fighter or a law enforcement officer. The inner end of the support arm is connected with the helmet. When the outer end of the support arm is closed (clamped) on a portion of the earcup, the earcup is connected with and supported on the helmet. When, the outer end of the support arm is opened (released), the earcup can be separated from the support arm and separated from the helmet for use in another manner, for example with a headband. In one embodiment, the support arm has a fixed length. In another embodiment, the support arm has an adjustable length.

SUMMARY OF THE INVENTION

A wireform attachment mechanism can be used to attach an earcup to a helmet. The outer end of the support arm can be opened to release the earcup, or closed to clamp onto the earcup.

BRIEF DESCRIPTION OF THE DRAWINGS

FIGS. 3A-3C are a set, of views of an upper piece that forms part of the support arm of FIG. 1;

DESCRIPTION OF EMBODIMENTS OF THE INVENTION

Figure 1:
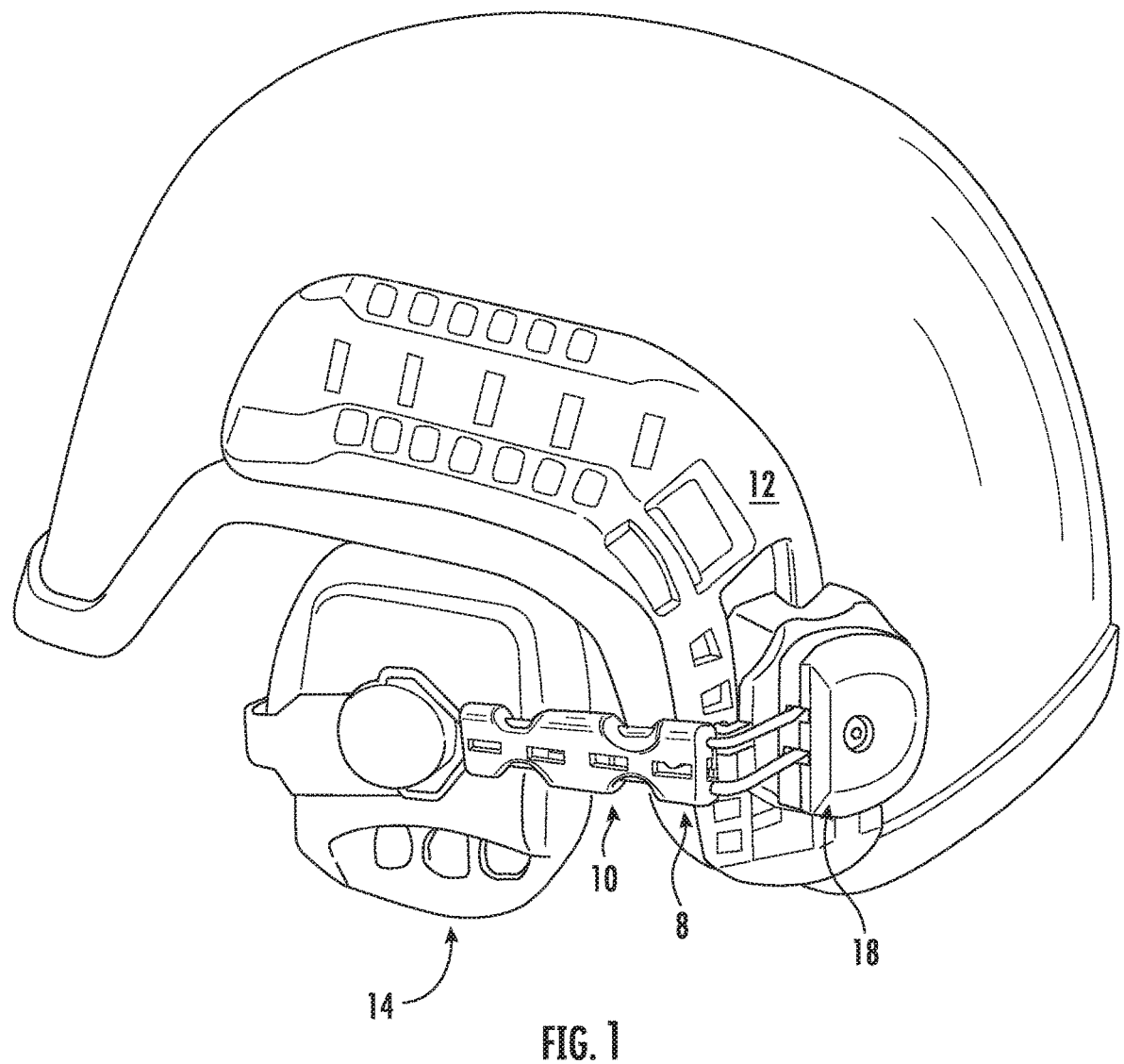
FIG. 1 is an illustration of an earcup suspension assembly including a support arm that is a first embodiment of the invention, shown assembled on a helmet and supporting an earcup.
Figure 2A:
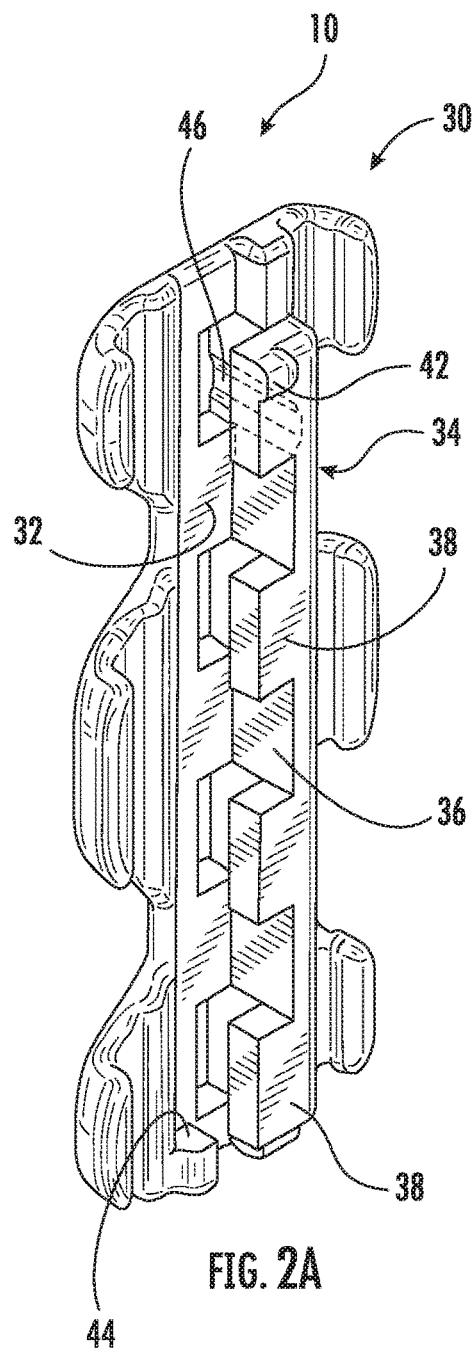
FIGS. 2A-2C are a set of views of a lower piece that forms part of the support arm of FIG. 1.
Figure 2B:
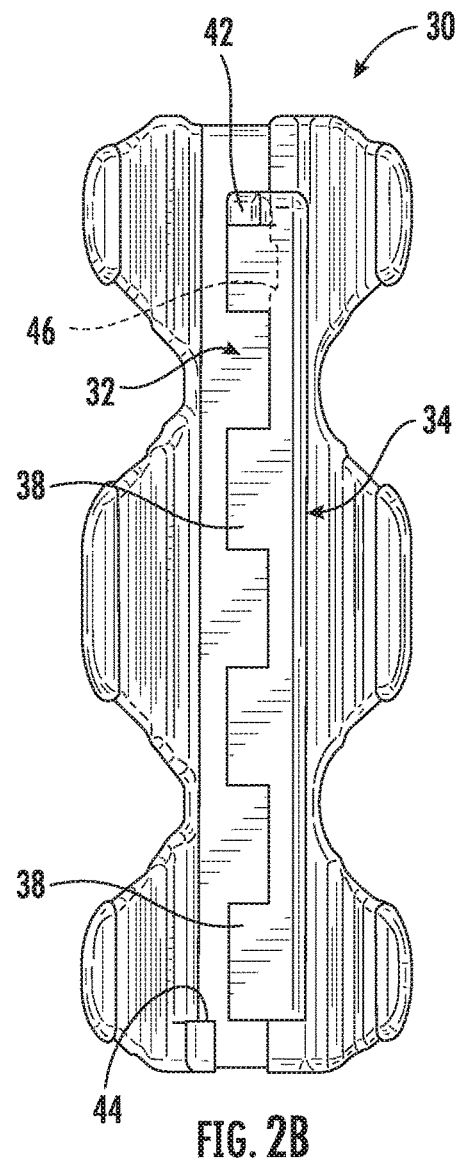
Figure 2C:
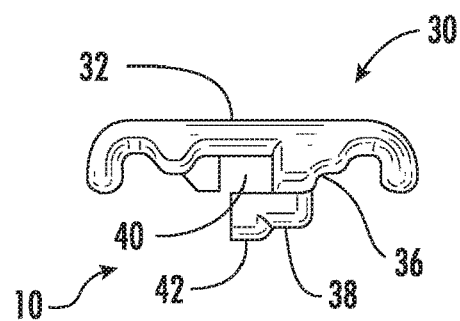

FIG. 1 illustrates an earcup suspension assembly 8 that includes a wireform attachment mechanism or support arm 10 that is a first embodiment of the invention. The assembly 8 is shown supported on a helmet 12. The helmet 12 could be of any configuration, and could be any head covering device. The particular helmet 12 that is illustrated does not have ear covering portions, thus allowing the assembly 8 to support earcups at a location outside of the enclosure of the helmet. The drawings show the helmet 12 as viewed from the left side; the right side is a mirror image, typically. Two earcup suspension assemblies 8 are commonly used with one helmet 12. Thus, the drawings focus on a left side earcup suspension assembly 8 that supports a left earcup 14; a right side earcup suspension assembly 8 could be a mirror image.

A rail connector is connected to a rail on the helmet 12. The support arm 10 is connected with the rail connector 18 in a manner not shown. The support arm 10 extends from the rail connector 18 to the earcup 14.

The support arm 10 includes three main elements: a wireform element 20, a lower piece 30, and an upper piece 50. The two pieces 30 and 50 are connected with each other in a position enclosing, and supported on, the wireform element 20. In one embodiment that has been constructed, the length of the wireform element 20 that extends from the rail connector is about 1 centimeters. The length of the pieces 30 and 50 is about 6 centimeters.

The wireform element 20 itself (FIG. 4) is made from metal wire about one to two millimeters in diameter and in this embodiment is a single piece. The wireform element 20 includes two parallel legs spaced apart from each other buy about one centimeter. At its outer end, the two legs extend outward then turn back inward and terminate in prongs 22 that face each other. The prongs 22 can be inserted into openings or bores in the earcup 14, specifically, in the disc of the earcup 14. When this is done, the earcup 14 is supported on the wireform element 20 for rotational movement about an axis that extends between the two prongs 22.

When the support arm 10 is in the closed or locked condition, the prongs 22 are, maintained securely in the disc and the earcup 14 is securely supported on the arm. The two pieces 30 and 50 are also slidable relative to each other, moving between a locked condition, and an unlocked condition, as described below in detail. In one embodiment that has been constructed, the two pieces 30 and 50 are movable relative to each other for about five millimeters (one half centimeter). The two pieces 30 and 50 form a control assembly that is secured onto the wireform element 20 and that is movable, as described below, between a first position blocking opening of the prongs 22 of the wireform element and a second position allowing the prongs to be opened.

Figure 4:
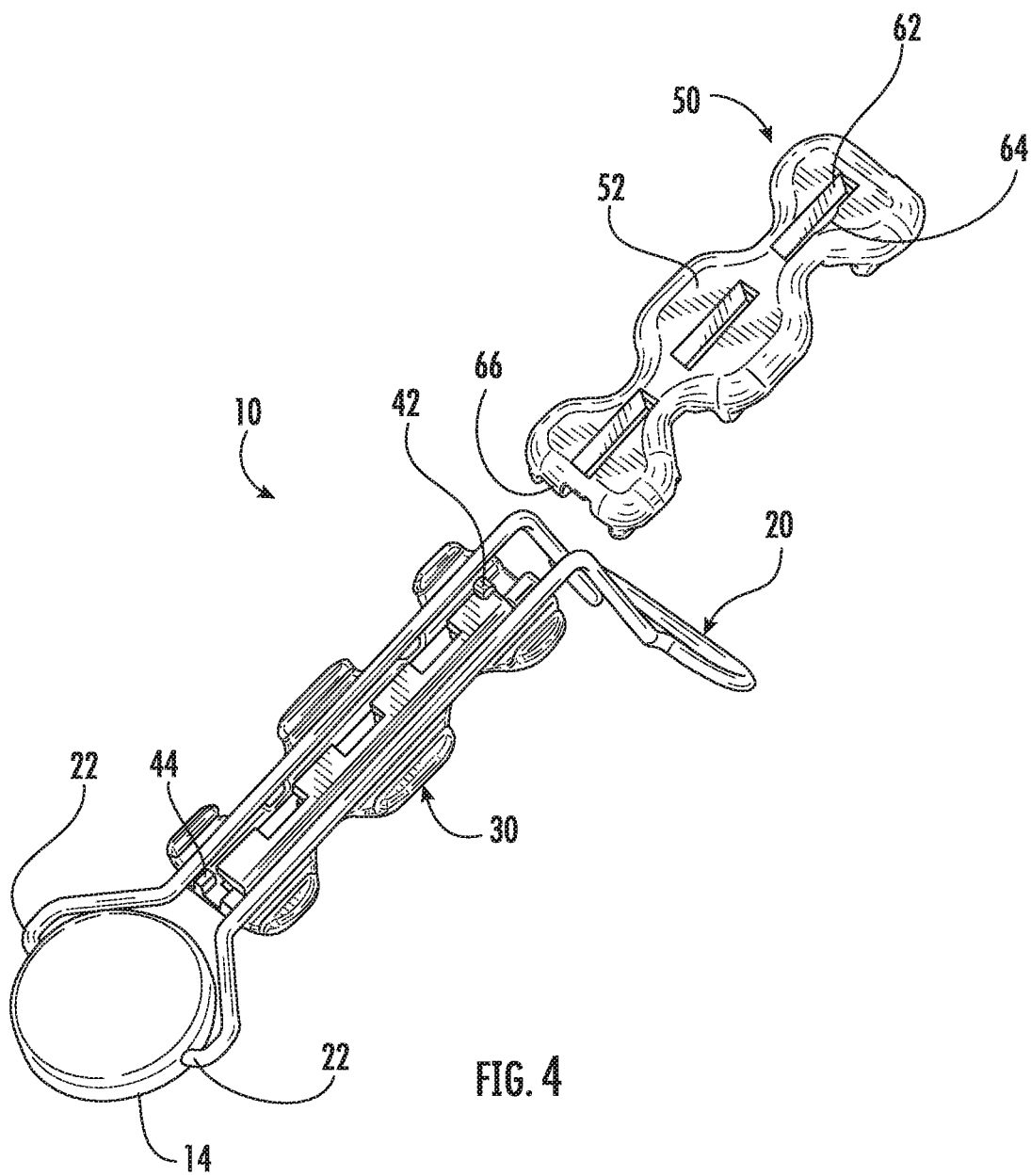
FIG. 4 is a perspective illustration of a step in the process of assembling the lower piece, of the upper piece, and of a wireform element that also is part of the support arm of FIG. 1.
Figure 5:
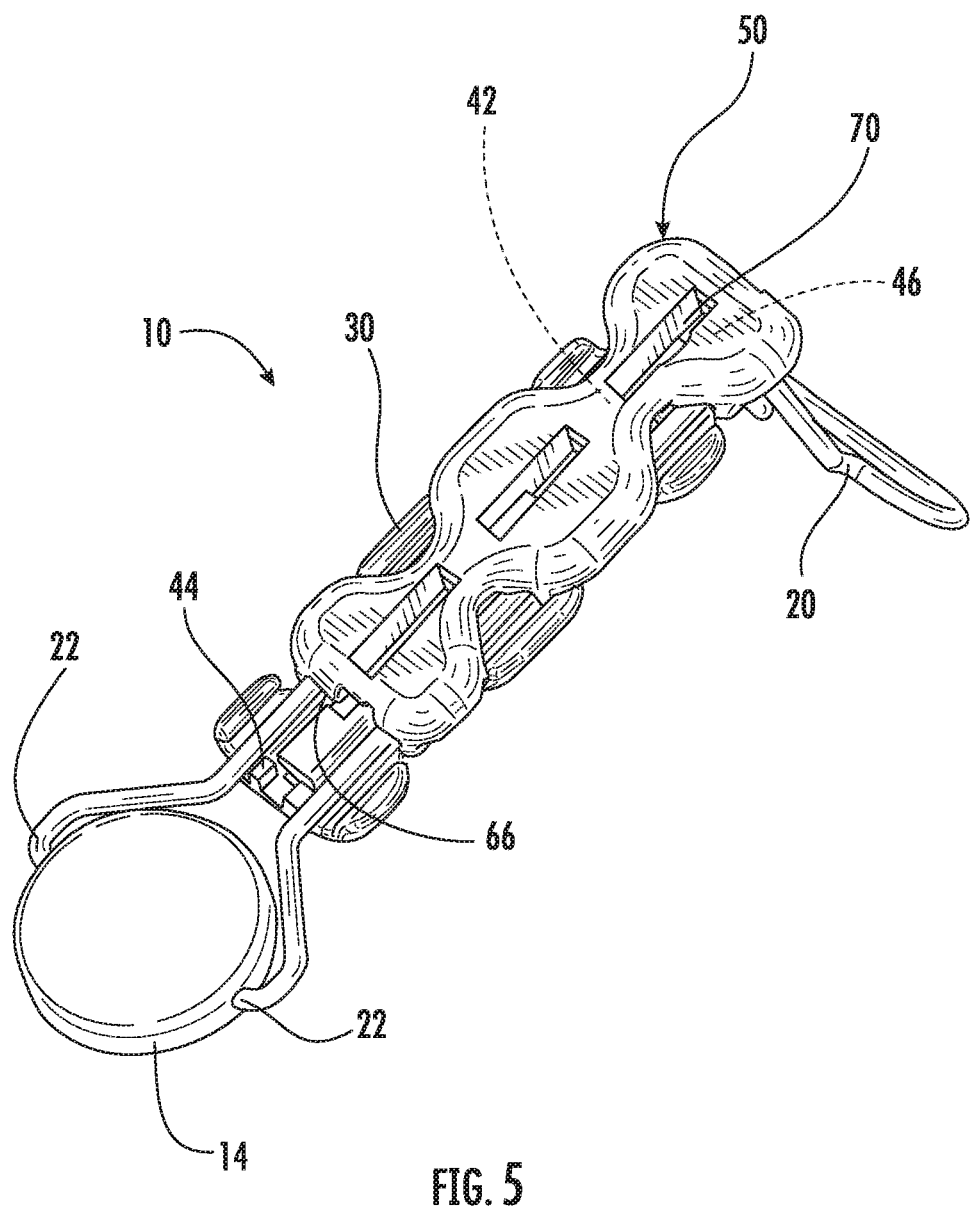
FIG. 5 show the support arm in n unlocked condition.
Figure 6:
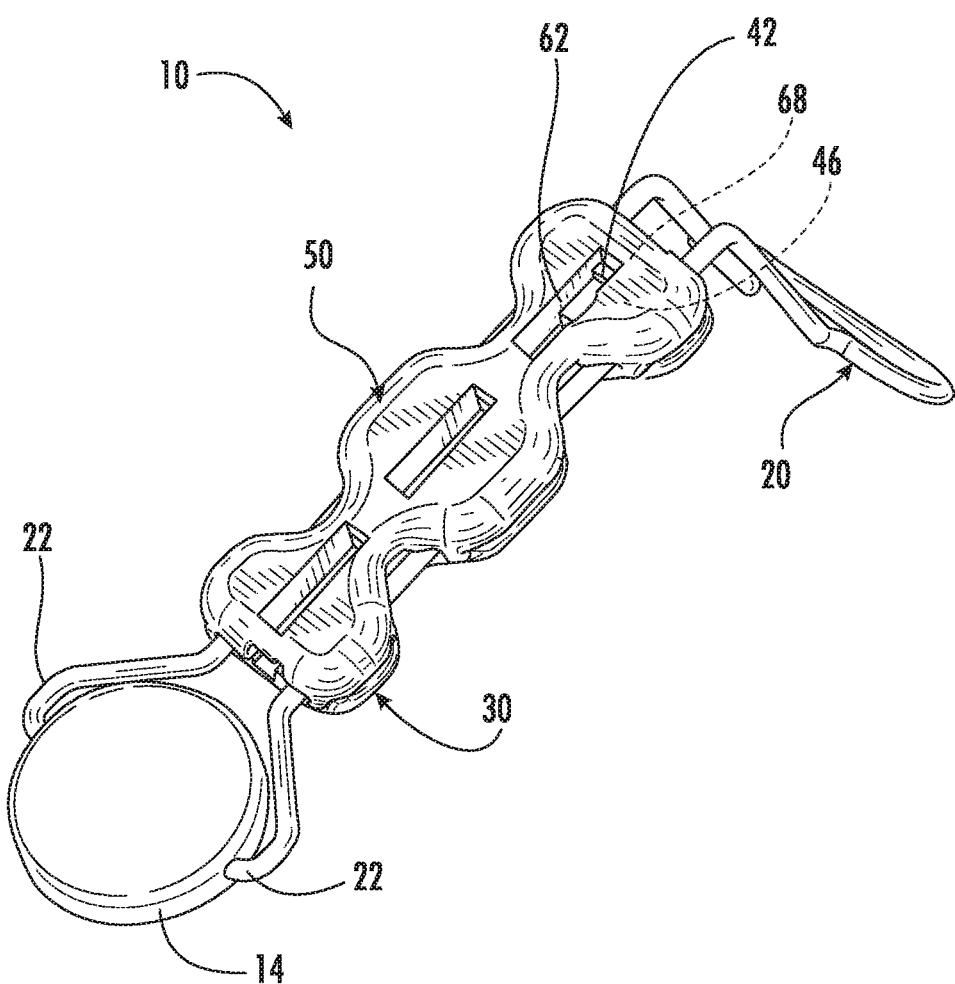
FIG. 6 shows the support arm in a locked condition.
Figure 7:
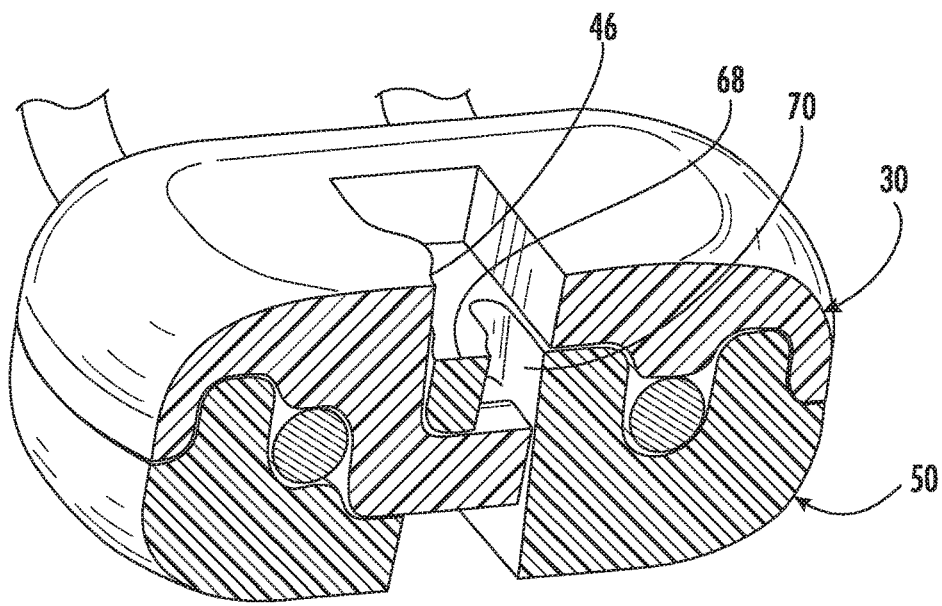
FIG. 7 is a fragmentary transverse sectional view of a portion of the support arm when in the locked condition.
Figure 8:
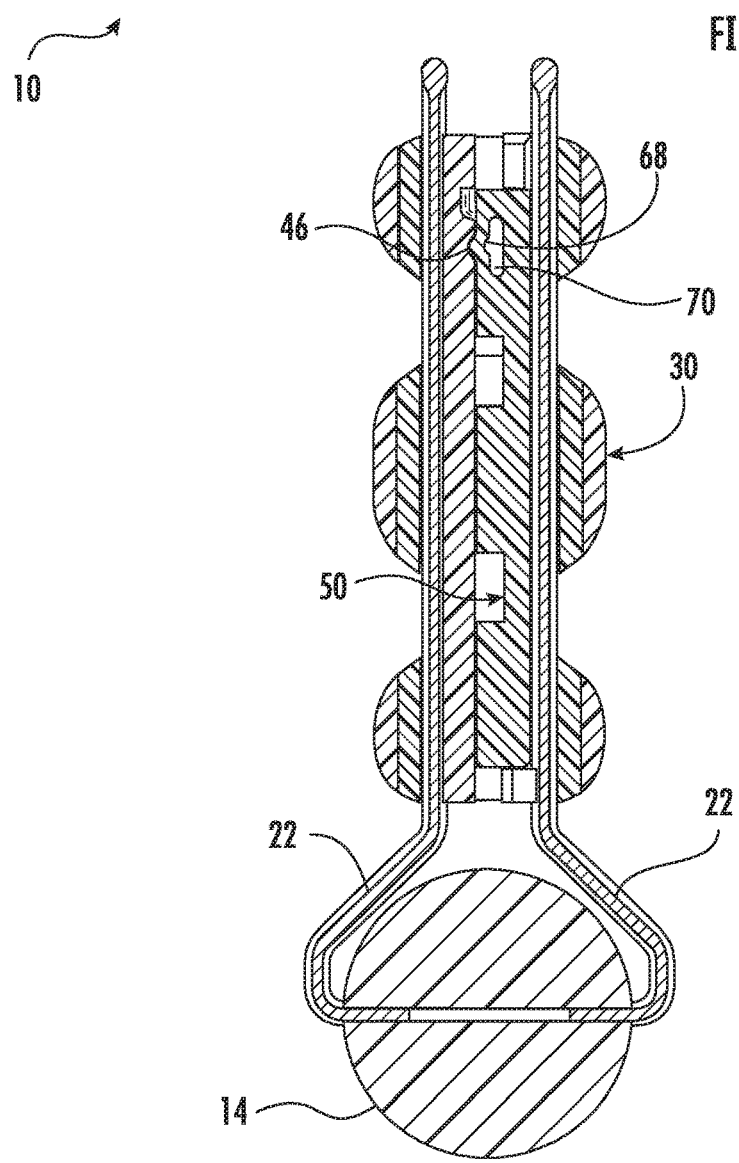
FIG. 8 is a longitudinal sectional view of the support arm when in the locked condition.

FIGS. 2-8 show the support arm 10, including the pieces 30 and 50, in more detail. In FIG. 6, the support arm 10 is in the locked condition, with the upper piece 50 overlying completely the lower piece 30. When the arm 10 is in the locked condition, the two prongs 22 are spaced about 11 to 12 millimeters apart and the relative positioning of the two pieces 30 and 50 prevents the prongs 22 from being spread farther apart.

In FIG. 5, the support arm 10 is shown in the unlocked condition, with the upper piece 50 having been slid for a small distance along and relative to the lower piece 30. When the arm 10 is in the unlocked condition, the two prongs 22 can be spread apart to a width of about 14 to 16 millimeters, to engage or release the earcup 14.

The upper and lower pieces 30 and 50 may be made from plastic. (The two pieces 30 and 50 are designated herein as the "upper piece 50" and the "lower piece 30", to distinguish them from each other, simply in relation to the drawings that are provided in this application. Obviously those identifiers can change depending on the location and orientation of the support arm 10.)

The lower piece 30 (FIGS. 2A-2C) has a generally planar main wall 32 with ribs and edge portions that are configured to mate with similar ribs and edge portions on the upper piece 50 and to facilitate sliding movement and retention of the two pieces 30 and 50 on the wireform element 20. The lower piece 30 has an L-shaped projection 34 including a vertical leg 36 that extends upward from the center of main wall 32 (up out of the plane of the paper as viewed in FIG. 2B) and a horizontal leg 38 that extends laterally from the outer end of the vertical leg (to the left as viewed in FIGS. 2A and 2B. A channel 40 is thereby formed between the horizontal leg 38 and the main wall 32.

There are several structural features on the lower piece 30 for controlling movement and positioning of the lower piece relative to the upper piece 50.

The first feature is a ramped boss 42, located at the top end (as viewed in FIG. 2A) of the horizontal leg 38 of the L-shaped projection 34. The ramped boss 42 projects outward from the horizontal leg 38, in a direction away from the main wall 32 of the lower piece 30. The boss 42 is ramped at its upper end (to the top as viewed in FIG. 2A) to facilitate sliding assembly of the lower piece 30 with the upper piece 50. The boss 42 cooperates with the upper piece 30, in a manner described below, to limit outward (opening) movement of the two pieces 30 and 50.

A second feature on the lower piece 30 is a bump stop 44 at the lower end of the second piece (by the prongs 22). The bump stop 44 cooperates with the upper piece 30, in a manner described below, to limit inward (closing) movement of the two pieces 30 and 50.

A third feature on the lower piece 30 is a pocket 46. The pocket 46 extends through the main wall 32 and also along the side surface 44 of the vertical leg 36 of the L-shaped projection 34. The pocket 46 cooperates with the upper piece 30, in a manner described below, to releasably hold the two pieces 30 and 50 in the closed position.

The upper piece 50 (FIGS. 3A-3C) has a generally planar main wall 52 with ribs and edge portions that are configured to mate with the lower piece 30 and to facilitate sliding movement and retention of the two pieces 30 and 50 on the wireform element 20. The upper piece 50 has an L-shaped projection 54 including a vertical leg 56 that extends downward from the center of the main wall 52 (up out of the plane of the paper as viewed in FIG. 3B) and a horizontal leg 58 that extends laterally from the outer end of the vertical leg (to the left as viewed in FIG. 3B). A channel 60 thus is formed between the horizontal leg 58 and the main wall 52.

There are several structural features on the upper piece 50 for controlling movement and positioning of the upper piece relative to the lower piece 30.

The upper piece 50 has a window 62 in the main wall 52. The window 62 has an end surface 64 that cooperates with the ramped boss 42 on the lower piece 30, in a manner described below, to limit outward (opening) movement of the two pieces 30 and 50.

Another feature on the upper piece 50 is a stop surface 66 on the end of the L-shaped projection 54. The stop surface 66 cooperates with the upper piece 30, in a manner described below, to limit inward (closing) movement of the two pieces 30 and 50.

Another feature on the upper piece 50 is a detent in the form of a triangular bump 68 that is formed on the horizontal leg of the L-shaped projection 54. The bump 68 extends laterally from the horizontal leg 58. Behind the bump 68 is formed an opening 70. The bump 68 cooperates with the pocket 46 on the lower piece 30 to releasably hold the two pieces 30 and 50 in the closed position, as described below.

When the upper piece 50 is assembled with the lower piece 30, the upper piece 50 overlies the lower piece 30, and both pieces 30 and 50 surround and together capture the two legs of the wireform element 20. The assembled upper piece 50 and lower piece 30 may be movable together for a small distance along the length of the legs of the wireform element 20.

FIGS. 4 and 5 illustrate an initial step in the assembly of the upper piece 50 with the lower piece 30 and the wireform element 20. The lower piece 30 may first be assembled with the wireform element 20. Then, the upper piece 50 may be slid longitudinally (down and to the left as viewed in FIG. 4) onto and into engagement with the lower piece 30 and the wireform element 20.

As this sliding movement continues, the parts eventually rove into an unlocked condition as shown in FIG. 5. In this condition, the wireform element 20 is captured between the upper piece 50 and the lower piece 30. The horizontal leg of the L-shaped projection 54 on the upper piece 50 is engaged in, and slides along, the channel 40 that is over the L-shaped projection 34 of the lower piece 30.

At the same time, the horizontal leg 38 of the L-shaped projection 34 of the lower piece 30 is engaged in, and slides along, the channel 60 that is under the L-shaped projection 54 of the upper piece 50. The ramped boss 42 on the lower piece 30 is in engagement with the end surface 64 of the window 62 in the main wall 52 of the upper piece 50.

When the support arm is in the unlocked condition, the spacing of the upper piece 50 longitudinally away from the lower piece 30 enables the two prongs 22 of the wireform element 20 to be moved apart from each other by a distance sufficient to release the disc of the earcup 14. As a result, the earcup 14 can be removed from the support arm 10 and, consequently, from the helmet.

The parts can then be moved into the locked condition shown in FIG. 6. To accomplish this, the upper piece 50 is slid further along the lower piece 30. The stop surface 66 on the upper piece 50 engages the bump stop 44 on the lower piece 30 to stop the relative sliding movement of the upper piece and the lower piece, in the closed condition.

As this relative closing movement occurs, the bump 68 (FIGS. 7 and 8) on the upper piece 50 slides along in engagement with the side wall of the vertical leg 36 of the L-shaped projection 34 of the lower piece 30. This sliding movement adds a desired amount of tension or resistance to the sliding movement. When the parts reach the closed condition, the bump 68 on the upper piece 50 moves into the pocket 46 on the lower piece 30. The engagement of the bump 64 in the pocket 46 releasably maintains the two pieces 30 and 50 in the locked or closed condition.

When the support arm 10 is in the locked condition, the two prongs 22 of the wireform element 20 are prevented from moving apart from each other by a distance that is sufficient to release the disc of the earcup 14. As a result, the earcup 14 is securely retained on the support arm 10 and, consequently, on the helmet 18.

The locking process is reversed to enable release of the earcup 14 from the support arm 10. When the parts are fully opened, the ramped boss 42 on the lower piece 30 engages the lower end surface 64 of the window 62 on the upper piece 50, to limit the outward (opening) movement) and thus keep the pieces together.

FIGS. 9-19 illustrate a wireform attachment mechanism or support arm 100 that is a second embodiment of the invention. In this embodiment, the wireform element comprises two separate wire pieces that are movable relative to each other; thus, the overall length of the support arm 100 is adjustable. In contrast, the first embodiment support arm has only one wire element that extends through and out both ends and so is fixed in overall length.

Specifically, the arm 100 includes two separate wireform elements that are longitudinally movable relative to each other to adjust the overall length of the arm 100. One wireform element 102 has a loop end and is connected with the rail connector, like the loop end of the element 20 of the first embodiment. The other wireform element 104 has prong ends and is connected with the earcup, like the prong end of the element 20 of the first embodiment. A total of three separate plastic pieces interconnect the two wireform elements, and allow for positioning and relative movement between them. The three pieces form a control assembly that is movable between a first position blocking opening of the prong ends of the wireform element and a second position allowing the prong ends of the wireform element to be opened.

Thus, the arm 100 includes generally five pieces: A loop wire 102, and a loop slider 110; an earcup wire 104, and an earcup slider 120; and a release tab 130. The loop slider 110 (FIG. 11) is a plastic piece that fixedly receives the inner end of the loop wire 102. The loop slider 110 has a generally C-shaped or U-shaped configuration including a main wall 112, opposite side walls 114, and channel tabs projecting 116 inward from the side walls. Channels 118 in the loop slider 110 are defined between the channel tabs 116 and the main wall 112.

The inner end of the loop wire 102 is fixedly captured on the inside of the main wall 112 of the loop slider 110. Thus, the loop wire 102 moves with the loop slider 110. The outer end of the loop wire 102 is formed as a loop that can be captured in the rail connector (FIG. 1).

The earcup slider 120 (FIGS. 12-15) is a plastic piece that slidably receives the inner end of the earcup wire 104. The earcup slider 120 has a generally flat configuration including a main body portion 122 and side rails 124 that project outward from opposite sides of the main body portion. The side rails 124 are configured and dimensioned to fit into the channels 118 of the loop slider 110.

The inner end of the earcup wire 104 is slidably captured in a chamber 126 on the inside of the main wall 122 of the earcup slider 120. Thus, the earcup wire 104 normally moves with the earcup slider 120, but can, as described below, move relative to the earcup slider to enable the earcup wire releasably engage and disengage from the earcup disk (FIG. 1) as in the first embodiment described above.

The release tab 130 is a narrow, elongate plastic piece that is slidable along the length of the earcup slider 104 under manual force applied by the user. The release tab 130 has a closed position retention hook 132 near its outer end (to the right as viewed in FIGS. 17-19). The release tab 130 has an open position retention hook 134 at its inner end (to the left as viewed in FIGS. 17-19). The outer end of the release tab 130 projects from the earcup slider 120.

When the parts are assembled, the loop wire 102 is fixedly captured in the loop slider 110. The earcup wire 104 has its inner end pushed into the chamber 126 in the earcup slider 120. The inner end of the release tab 130 is pushed in between the two legs of the earcup slider 120 that are in the chamber 126 and engages the inner end of the earcup wire 104.

The earcup slider 120 is fitted into the loop slider 110. The rails 124 on the earcup slider 120 are fitted into the channels 118 on the loop slider 110. In this position, the earcup slider 120 is movable (slidable) relative to the loop slider 110, for a limited, controlled distance, to adjust the overall length of the support arm 100.

Figure 9:
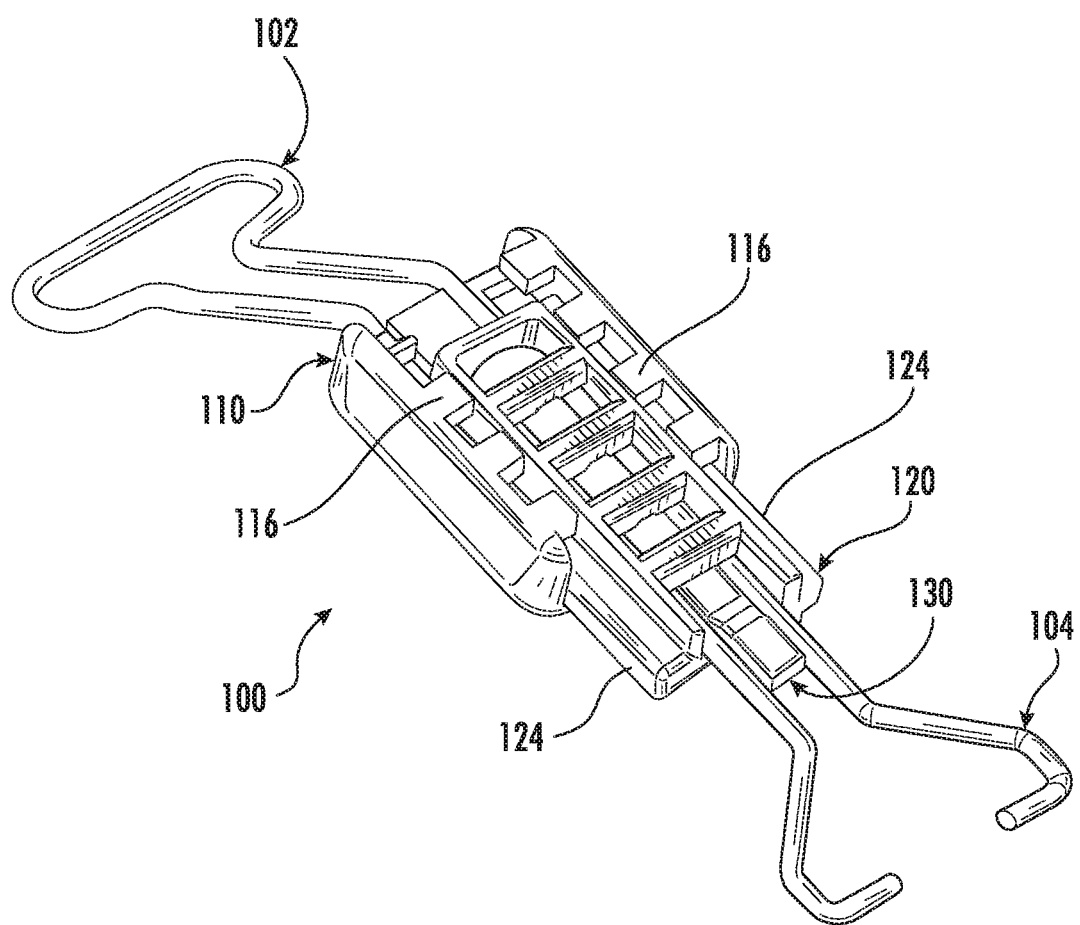
FIG. 9 is an illustration of a support arm that is a second embodiment of the invention, being adjustable in length, shown in an extended length condition with the earcup connector locked.

FIG. 9 illustrates the earcup slider 120 pulled out as far as possible from the loop slider 110. In this position, a stop surface 140 on the loop slider 110 (FIG. 15) engages a stop surface 142 on the earcup slider 120 to block further outward movement, and sets the greatest extended length of the support arm 100.

Figure 10:
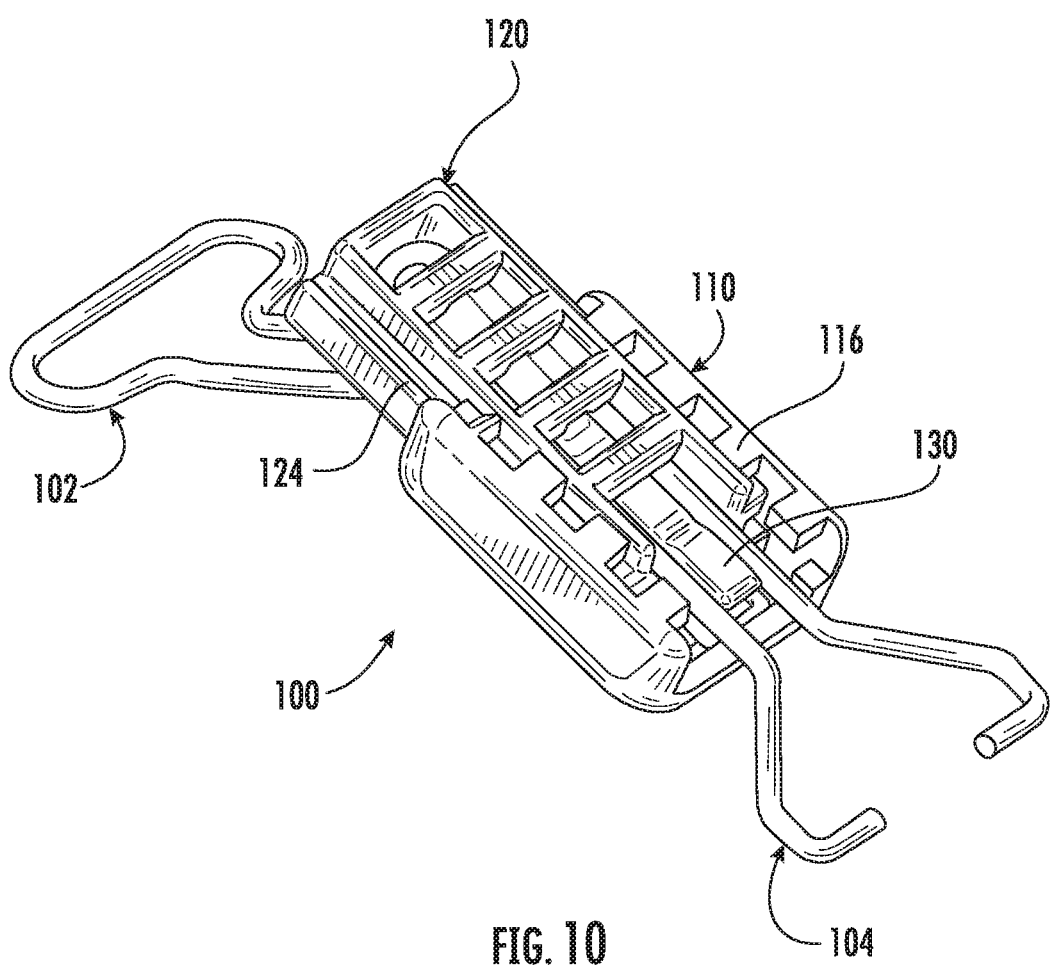
FIG. 10 is a view showing the support arm of FIG. 9 in a shortened length.
Figure 11:
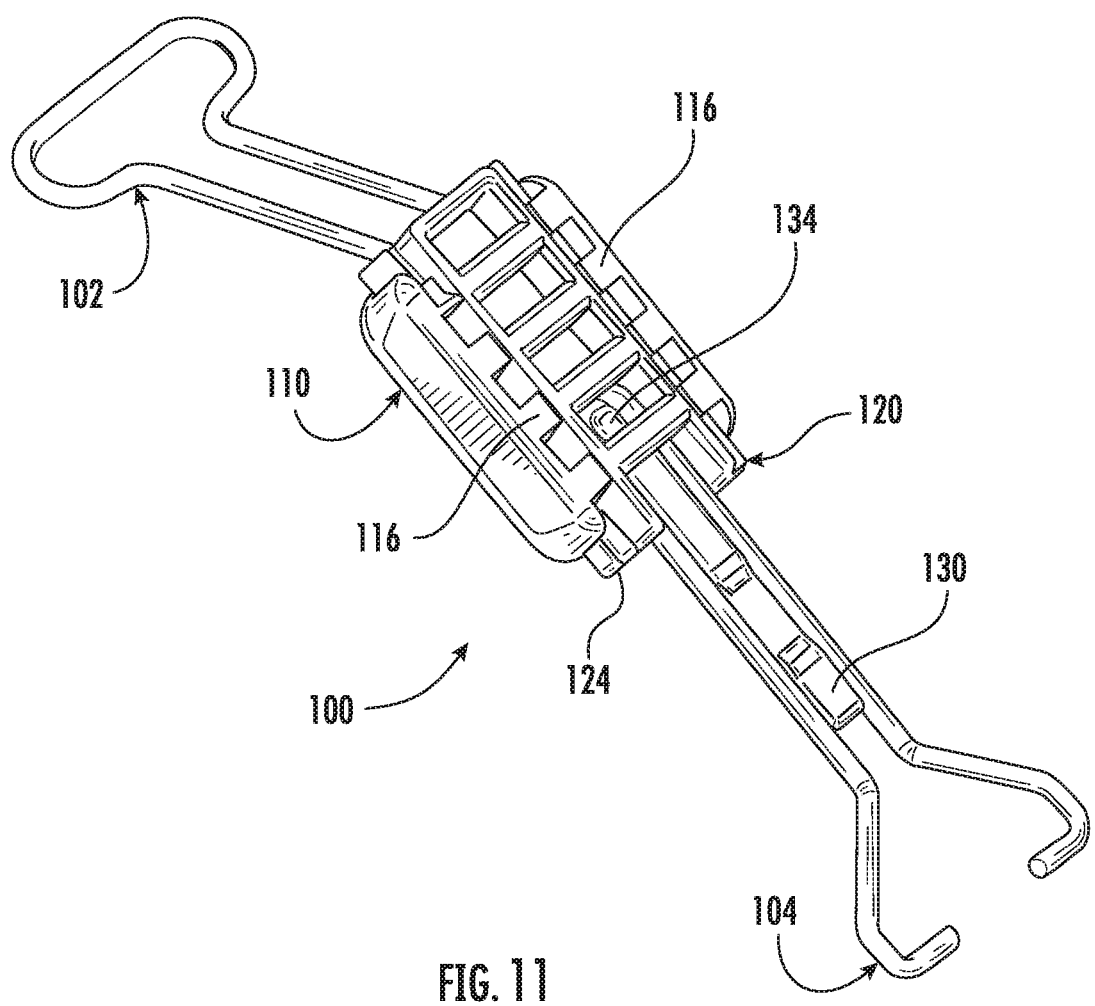
FIG. 11 is a view showing the support arm of FIG. 9 in an intermediate length with the earcup connector unlocked.
Figure 12:
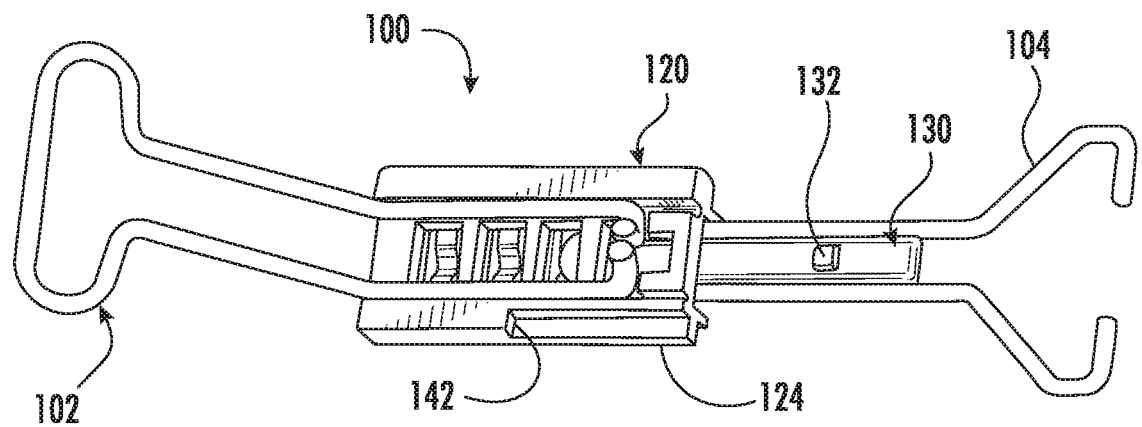
FIG. 12 is an illustration of certain parts only of the support arm of FIG. 9.
Figure 13:
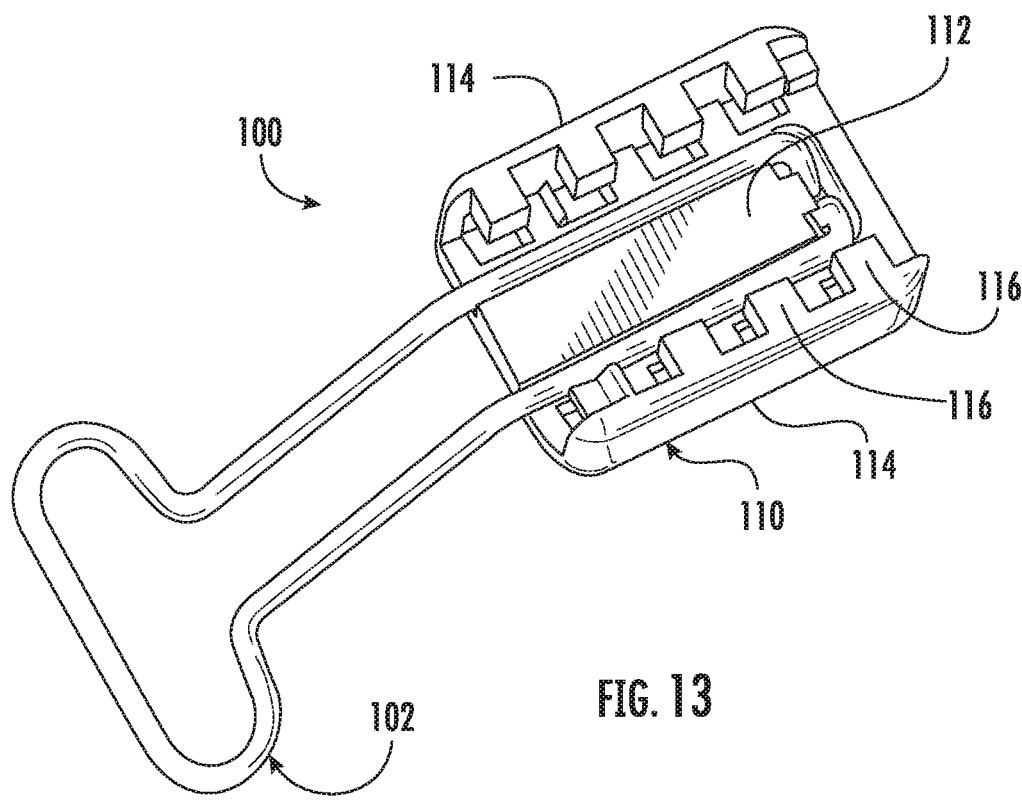
FIG. 13 is an illustration of certain parts only of the support arm of FIG. 9.
Figure 14:
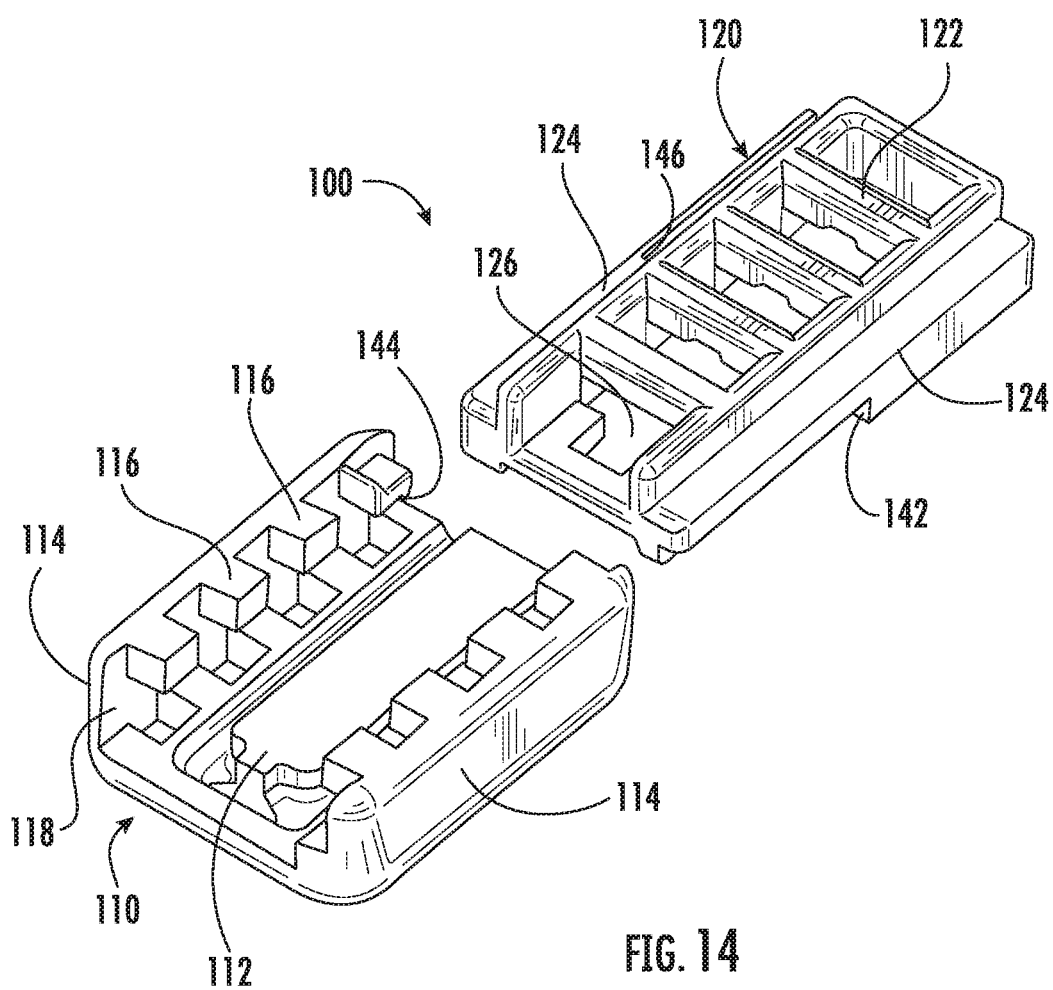
FIG. 14 is an illustration of certain parts only of the support arm of FIG. 9.
Figure 15:
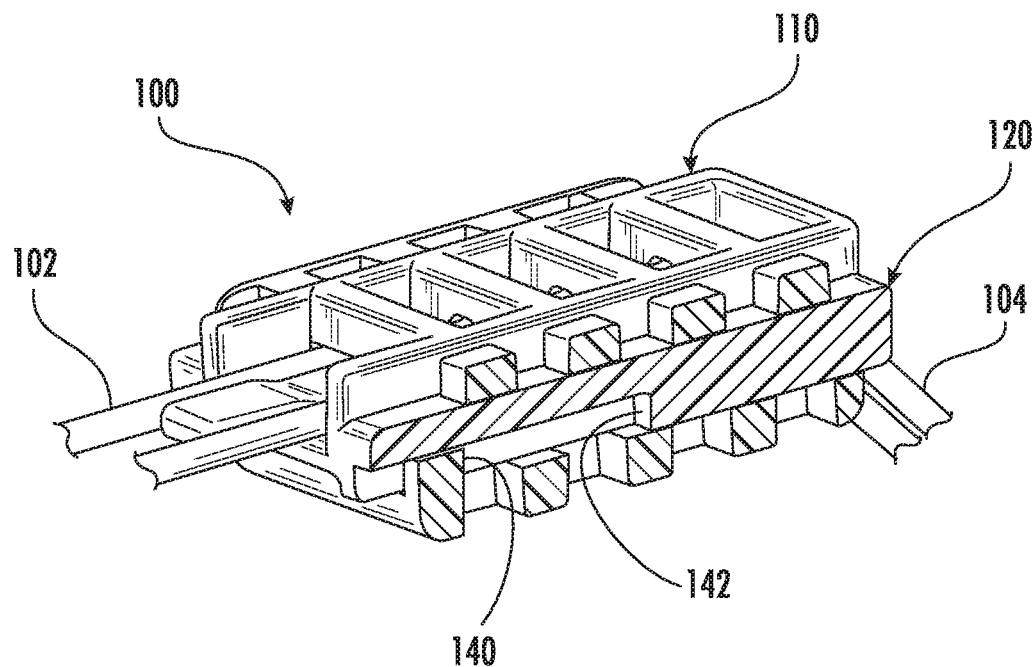
FIGS. 15 and 16 illustrate the action of stop surfaces that limit relative movement of the parts of the support arm of FIG. 9.
Figure 16:
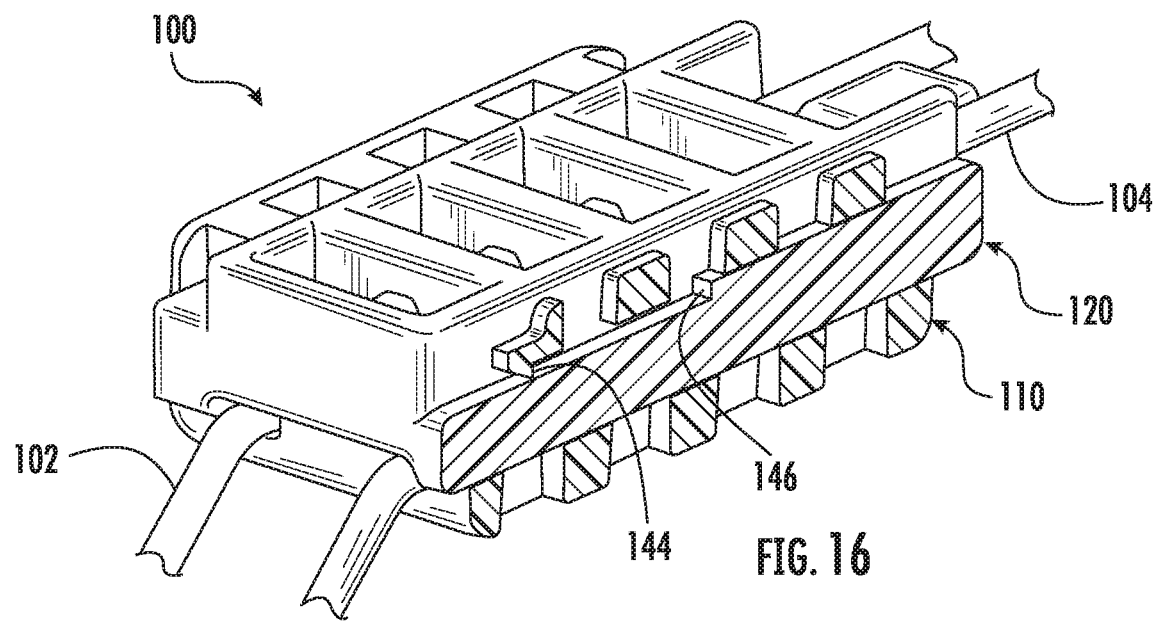

FIG. 10 illustrates the earcup slider 120 closed up as much as possible from on the loop slider 110. In this position, a stop surface 144 on the loop slider 110 (FIG. 16) engages a stop surface 146 on the earcup slider 120 to block further inward movement, and set the shortest available length of the support arm 100.

The relative dimensions of the rails 124 on the earcup slider 120 and the channels 118 on the loop slider 110 are selected to provide an interference fits between the rails and the channels. Thus, the two sliders 102 and 104 will stay in whatever relative position is set, until the user manually pushes them apart or together.

Figure 17:
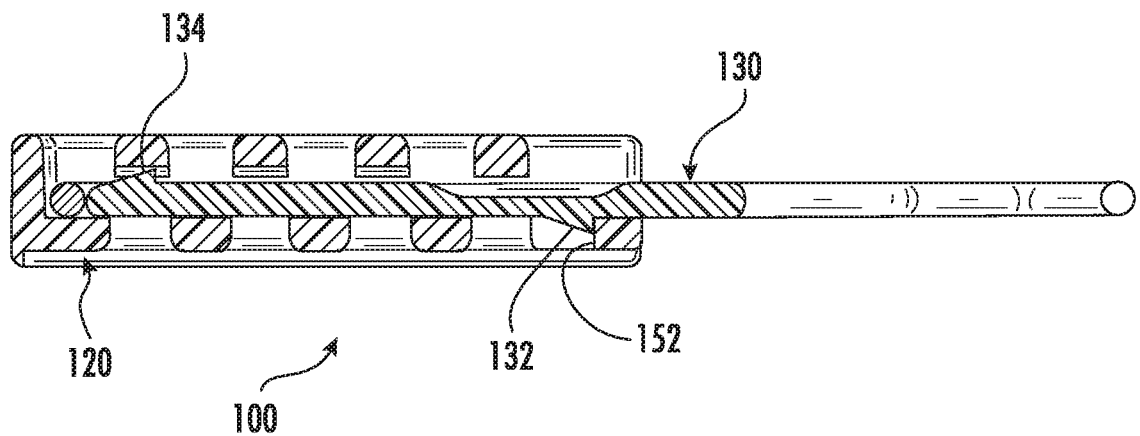
FIGS. 17-19 are views illustrating the unlocking of the support arm of FIG. 9.
Figure 18:
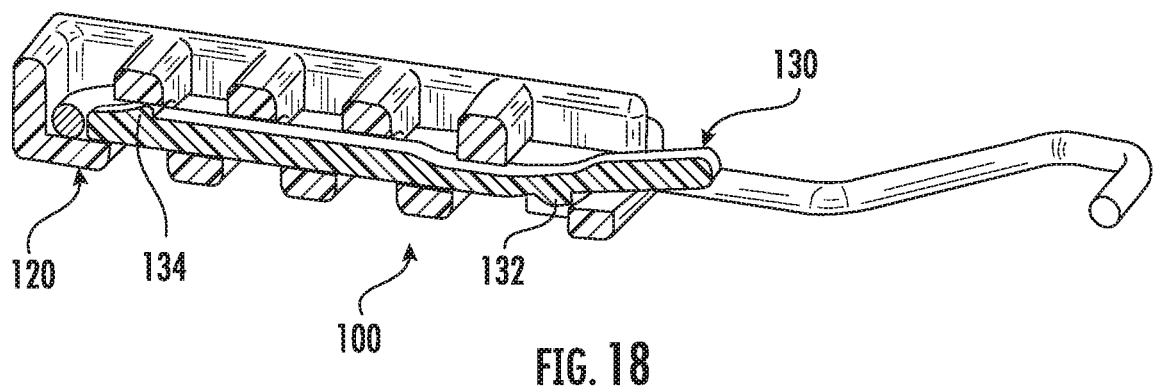
Figure 19:
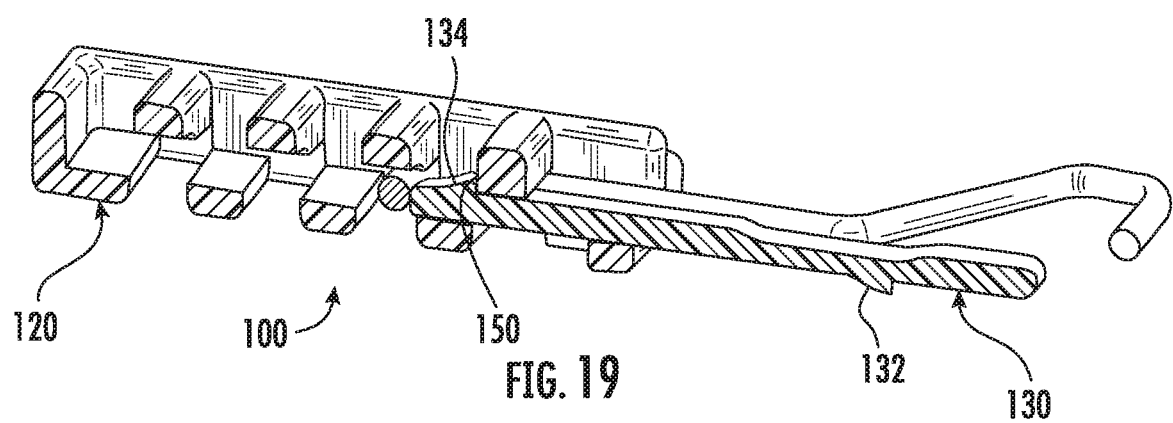

No matter which length the support arm 100 is set at, the earcup wire 104 is selectively releasable to enable disconnection of the support arm from the earcup disc. This release is effected by pulling the release tab 130 out of the earcup slider 120 in a manner as illustrated in FIGS. 17-19. Specifically, the projecting outer end of the release tab 130 is lifted upward (as viewed in FIG. 17), freeing the closed position retention hook 132 from engagement with the end wall on the earcup slider 120. The release tab 130 can then be pulled out of the earcup slider 120 as shown in FIGS. 18 and 19. The open position retention hook 134 on the release tab 130 engages a stop surface 150 on the earcup slider 120 to limit outward movement of the release tab 130. In this open position of the parts, the earcup wire 104 is freed to move out from the earcup slider 120, to enable the prongs of the earcup wire 104 to be opened.

To close the support arm 100, the earcup wire 104 and the release tab 130 are pushed back into the loop slider 110, to the position shown in FIG. 17. Again, the closed position retention hook 132 engages a stop surface 152 on the earcup slider 120 to hold the parts in the closed position.

The invention claimed is:

1. A support arm for use in supporting an earcup on a helmet, comprising:
   a wireform element having an inner end portion that is connectable with the helmet;

the wireform element having an outer end portion that can be selectively closed to clamp onto the earcup to keep the earcup supported on the helmet, and that can be selectively opened to enable release of the earcup from the helmet, and a control assembly of at least two parts that are secured onto the wireform element and that are movable relative to each other and relative to the wireform element between a first position blocking opening of the outer end portion of the wireform element and a second position allowing the outer end portion of the wireform element to be opened.

2. A support arm as set forth in claim 1 wherein the wireform element is a single piece that extends through and from opposite ends of the control assembly, the support arm having a fixed overall length.

3. A support arm as set forth in claim 2 wherein the inner end portion of the single piece wireform element is a loop configured for connection with the helmet, and the outer end portion includes two ends of the single piece wireform element that are formed as prongs that can selectively clamp onto the earcup to support the earcup with in the closed position.

4. A support arm as set forth in claim 3 including stop features far limiting opening and closing movement of the control assembly.

5. A support arm as set forth in claim 1 wherein the w reform element is formed as first and second separate wire pieces that extend from opposite ends of the control assembly, the support arm thereby having a variable overall length.

6. A support arm as set forth in claim 5 wherein the overall length of the support arm is varied by moving first and second parts of the control assembly relative to each other; and the control assembly is movable to the second position by moving a third part of the control assembly relative to the first and second parts of the control assembly to allow the outer end portion of the wireform element to be opened.

7. A support arm as set forth in claim 6 wherein the first part of the control assembly is fixed for movement with the first wire piece, and the second part of the control assembly movably supports the second wire piece, and the third part of the control assembly constitutes a release tab that is supported on the second part of the control assembly for movement relative to the second part thereby to enable movement of the second wire piece relative to the second part thereby to adjust the overall length of the support arm.

* * * * *